United States Patent [19]
Jackson et al.

[11] 4,435,506
[45] Mar. 6, 1984

[54] ISOLATION OF SUPEROXIDE DISMUTASE

[75] Inventors: David E. Jackson, Bourbonnais; Frank J. Mannuzza, Peotone, both of Ill.

[73] Assignee: Miles Laboratories, Inc., Elkhart, Ind.

[21] Appl. No.: 408,038

[22] Filed: Aug. 13, 1982

[51] Int. Cl.³ .......................... C12N 9/02; C12N 9/08
[52] U.S. Cl. ................................. 435/189; 435/814; 435/192
[58] Field of Search .............................. 435/189, 192; 260/112 R

[56] References Cited

U.S. PATENT DOCUMENTS

| 3,579,495 | 5/1981 | Huber | 260/115 |
| 3,813,289 | 5/1974 | Huber et al. | 195/4 |
| 4,341,867 | 7/1982 | Johansen | 435/189 |
| 4,346,174 | 8/1982 | Yasuda | 435/189 |
| 4,388,406 | 6/1983 | Johansen | 435/189 |
| 4,390,628 | 6/1983 | Johansen | 435/189 |

Primary Examiner—Lee M. Shapiro
Attorney, Agent, or Firm—James D. McNeil

[57] ABSTRACT

A method for isolating superoxide dismutase. The method involves contacting red blood cells containing proteinaceous impurities with a water-miscible organic solvent at a pH in the range of 5 to 8 and a temperature of from 15° to 50° C., removing the impurities and obtaining purified superoxide dismutase.

7 Claims, No Drawings

ISOLATION OF SUPEROXIDE DISMUTASE

BACKGROHND OF THE INVENTION

1. Field of the Invention

In 1939 a copper-containing protein was isolated from erythrocytes and found to be one of a family of water-soluble metalloprotein congeners. These proteins have been assigned the non-proprietary name "orgotein" by the U.S. Adopted Name Council. It was later determined that these proteins possessed enzymatic activity which catalyzed the reaction $$O_2^- + O_2^- + 2H^+ \rightarrow H_2O_2 + O_2$$

An alternate name, superoxide dismutase, was proposed for these proteins, because they dismuted superoxide radicals to peroxide and molecular oxygen. It is theorized that superoxide dismutase may perform a role in protecting cells from the toxic effects of physiologically produced superoxide radicals, and against the deleterious effects of ultraviolet radiation.

2. Description of the Prior Art

U.S. Pat. No. 3,579,495 describes a method for isolating orgotein from red blood cells. The method disclosed therein involves first removing hemoglobin from the lysed red blood cells by precipitating the hemoglobin with an organic solvent at a temperature of 5° to −15° C. and a pH of from 5 to 8. The organic solvent is a water-immiscible solvent. The patentees indicate that halogenated solvents, e.g., methylene chloride and chloroform are preferred, and that a small amount of a water-miscible solvent can be added to increase the contact between the hemoglobin and the precipitating solvent. After precipitation of the hemoglobin, the hemoglobin is removed. The hemoglobin-free supernatant is then heated at 60° to 80° C. in the presence of a divalent metal cation such as $Mg^{++}$, $Cu^{++}$, or $Mn^{++}$, to remove proteinaceous impurities. The divalent metal cations are then removed and the isolated orgotein recovered from the supernatant.

U.S. Pat. No. 3,813,289 also describes a method for isolating orgotein from red blood cells. The method involves heating hemoglobin-containing red blood cells at a temperature of from 60° to 80° C. and a pH of from 5 to 8, to precipitate the hemoglobin. The precipitated hemoglobin is removed and the isolated orgotein removed from the supernatant. The patentees indicate that the advantage of this claimed process over the process claimed in U.S. Pat. No. 3,579,495 is that hemoglobin, which constitutes 99 percent of the proteins in red blood cells, is removed without the use of an organic solvent.

The method described in U.S. Pat. No. 3,579,495 and in U.S. Pat. No. 3,813,289 present technical difficulties in removing the proteinaceous impurities.

In the method described in U.S. Pat. No. 3,579,495, when the suspension is centrifuged, a three-phase system is produced. The upper phase is an aqueous phase containing orgotein; the middle phase contains the proteinaceous impurities as a gelatinous material; and the lower phase is an organic phase.

In the method described in U.S. Pat. No. 3,813,289, when the suspension is centrifuged, a liquid phase containing the orgotein and an insoluble phase containing proteinaceous impurities are produced.

In both processes, the impurities are difficult to compact and difficult to remove.

Neither of the above references suggest or disclose that superoxide dismutase can be isolated from red blood cells by rapidly denaturing the hemoglobin and other proteinaceous impurities with a water-miscible organic compound wherein the proteinaceous impurities are compactible and easy to remove.

SUMMARY OF THE INVENTION

The present invention is directed to a method for isolating superoxide dismutase from red blood cells which contain proteinaceous impurities. The method involves contacting the red blood cells with a water-miscible organic solvent for a time sufficient to cause denaturing of the proteinaceous impurities. The pH is maintained in the range 5 to 8, and the temperature in the range 15° and 50° C. After the proteins are denatured, purified superoxide dismutase is recovered from the red blood cells.

DETAILED DESCRIPTION OF THE INVENTION

The red blood cells which are used as the starting material in the claimed method can be obtained from animals such as cattle, horses, goats, sheep, pigs, rabbits, chickens and humans. Bovine red blood cells are preferred, as bovine blood is readily available from slaughter houses. Fresh whole blood or whole blod stabilized with an anticoagulant to prevent clotting, can be used. The whole blood can be centrifuged to separate the red blood cells from the plasma. Such centrifugation may lyse the cells. Subsequent dilution with water and water-miscible solvent will achieve complete lysis.

The whole blood can be used as collected, or can be diluted with water to facilitate ease of handling. For example, addition of 3 volumes of water provides a red blood cell suspension which is easy to process.

Red blood cells contain only a small amount of superoxide dismutase. It is estimated that less than 0.1 percent (wt/wt basis) superoxide dismutase is present; the remaining 99.9 percent consists of unwanted proteinaceous components. Hemoglobin constitutes a major amount of the impurities.

A water-miscible organic solvent such as methanol, ethanol, propanol, isopropanol, or acetone, is then added to the red blood cells. From about 5 percent to 60 percent of solvent (v/v), based on the amount of diluted red blood cells present can be used. Because of its favorable cost and availability, solvents such as isopropanol are preferred. The pH is maintained in the range of 5 to 8. A preferred pH range is 5.5 to 6.5. Bovine red blood cells normally have a slightly basic pH; the pH can be adjusted to the range described above by addition of a mineral acid, e.g., $HCl$, $H_2SO_4$, $HNO_3$; HCL is preferred.

The red blood cells in the water-miscible organic solvent are maintained at temperature of from 15° to 50° C., for a time sufficient to cause denaturation of proteinaceous impurities present. Denaturation of the proteinaceous impurities is a time-temperature dependent phenomenon, and is also dependent upon the amount of red blood cells being processed. It has been determined that the denaturation can be achieved by maintaining the temperature at 50° C. for about 15 minutes to 1 hour, or can be achieved in a longer period of time by maintaining the temperature between about 15° C. to 35° C., for a time period of up to 48 hours.

Prior to denaturation, the red blood cell-water miscible organic solvent mixture has a deep red opaque appearance. As denaturation occurs, the mixture begins to separate into a solid and a liquid phase. The solid phase contains proteinaceous impurities; the liquid supernatant which contains superoxide dismutase in solution becomes a light gold color.

It has been determined that preferred conditions for isolating superoxide dismutase by the claimed method involve using a pH of 5.5 to 6.5 and a temperature of about 50° C. With the amount of red blood cells processed in Example 1, acceptable clarity was achieved in 15 minutes; maximum clarity of the supernatant was achieved in about 1 hour.

The resulting supernatant-solid phase which is produced during denaturation can be separated by conventional liquid-solid separation techniques, e.g., filtration or centrifugation. The proteinaceous impurities are easily compactible and can be readily removed by these techniques.

After separation, the superoxide dismutase is present in a small amount in a large volume of supernatant and it is necessary to concentrate the supernatant. Conventional techniques can be used, e.g., ultrafiltration, affinity chromatography, ion-exchange chromatography, or by precipitation techniques, for example by addition of ammonium sulfate or organic solvents such as acetone, or a combination of such techniques. A preferred method is ultrafiltration and precipitation.

Subsequent to concentration of the superoxide dismutase, the superoxide dismutase can be further purified by conventional techniques such as affinity chromatography, ion-exchange chromatography and gel filtration. These techniques help to remove any residual amount of organic solvent associated with the superoxide dismutase. The superoxide dismutase recovered has a purity in the range from 80 to greater than 95 percent.

EXAMPLE I

A 368 liter portion of fresh bovine red blood cells which had been separated from the plasma portion by centrifugation was collected at a slaughter house. The red blood cells were diluted with 1104 liters of water and mixed well. The pH of the red blood cells was about 7.1; approximately 31 liters of 1 N HCl were added to adjust the pH to 6.0. Total volume of the red blood cell mixture was 1503 liters.

For each liter of diluted red blood cells, 33 ml of 99 percent pure isopropanol was added. A total of 502 liters was added. The red blood cell-isopropanol solution was heated to 50° C. and held at that temperature for one hour, then cooled to 15° C. The proteinaceous impurities settled to the bottom as a dark red precipitate, leaving a light gold colored supernatant.

The precipitate was an easily compactible mass and was removed by filtration through cellulose filter media, using a plate and frame press. The volume of filtrate was 1202 liters and the precipitate, which was discarded, weighed 633 kg.

The filtrate containing superoxide dismutase was concentrated by ultrafiltering the liquid using hollow fiber cartridges, commercially available from Rohm and Haas, Kansas City, Missouri, under the trade designation Romicon PM-10.

Approximately 550 liters of concentrated filtrate was obtained. The filtrate was cooled to about 0 to 5° C. and 1.5 volumes of −5° acetone was added; total volume of acetone added was 825 liters. Following addition of the acetone, a precipitate formed which was rich in superoxide dismutase.

The acetone solution was mixed for about 3 hours and allowed to settle for 48 hours. The solution containing the superoxide dismutase precipitate was centrifuged at a high speed, low flow (13,000 g, 1.5 to 1.0 liters/minute).

The precipitate collected was determined to weigh 228 grams (wet weight). The precipitate was dissolved in a buffer solution of tris(hydroxymethyl)aminomethane (pH 7.0) and centrifuged to remove insoluble impurities. The semi-purified dissolved superoxide dismutase was chromatographed on cross-linked dextran. A final yield of 9 grams of superoxide dismutase was obtained.

The activity of the superoxide dismutase was determined by a method involving the aerobic reduction of nitro-blue tetrazolium by NADH in the presence of phenazine methosulfate. This reduction is inhibited by the superoxide dismutase enzyme. [See *Biochemie*, 57:657 (1975)]. One unit of superoxide dismutase is defined as that amount of enzyme which will cause a 50 percent inhibition in the rate of reduction of cytochrome C at 25° C. and a pH of 7.8[See *I. J. Biol. Chem.*, 224:6049 (1969)]. Based on this method of assay, a purity of 87 percent was achieved.

EXAMPLE II

A 970 liter portion of fresh bovine red blood cells which has been separated from the plasma portion by centrifugation was collected at a slaughter house. The red blood cells were diluted with 2910 liters of water and mixed well. The pH of the red blood cells was about 7.0; approximately 47 liters of 1 N HCl were added to adjust the pH to 6.0. Total volume of the red blood cell mixture was 3927 liters.

A total of 1318 liters of 99 percent pure isopropanol was added. The red blood cell-isopropanol solution was heated to 35° C. for about 12 hours, then cooled to 15° C. The proteinaceous impurities formed a precipitate, leaving a light gold color supernatant, containing the superoxide dismutase.

The precipitate was an easily compactible mass and was removed by filtration through cellulose filter media, using a plate and frame press. The precipitate was discarded and the supernatant was stored at −5° C. for future use.

One portion of the supernatant was concentrated to isolate superoxide dismutase by the procedure described in Example I. Based on the enzyme inhibition test described previously, the isolated superoxide dismutase was determined to have about 80 percent purity.

What is claimed is:

1. A method of isolating superoxide dismutase from red blood cells in the presence of proteinaceous impurities, which comprises contacting said red blood cells with a water-miscible organic solvent, at a pH in the range of 5 to 8, and a temperature of from 15° to 50° C. to denature said impurities, removing said impurities and obtaining therefrom purified superoxide dismutase.

2. A method as claimed in claim 1 wherein the water-miscible organic solvent is selected from the group consisting of methanol, ethanol, propanol, isopropanol, and acetone.

3. A method as claimed in claim 2 wherein the water-miscible organic solvent is isopropanol.

4. A method as claimed in claim 1, wherein the pH is from 5.5 to 6.5.

5. A method as claimed in claim 1, wherein the temperature is about 50° C.

6. A method as claimed in claim 1, wherein the time required for denaturing said proteinaceous impurities is from 15 minutes to 48 hours.

7. A method of isolating superoxide dismutase from red blood cells in the presence of proteinaceous impurities which comprises the steps of contacting said red blood cells with isopropanol for about 15 minutes, at a pH of about 6.0 and a temperature of about 50° C., to cause denaturation of said impurities and the formation of a solid phase and a liquid phase, said liquid phase containing superoxide dismutase, separating said solid and liquid phase, concentrating said liquid phase and obtaining therefrom purified superoxide dismutase.

* * * * *